(12) United States Patent
Yaguchi et al.

(10) Patent No.: US 7,850,707 B2
(45) Date of Patent: Dec. 14, 2010

(54) ULTRASONIC SURGERY APPARATUS

(75) Inventors: Shigeo Yaguchi, Ota-ku (JP); Hidenori Kanda, Okazaki (JP)

(73) Assignee: Nidek Co., Ltd., Aichi-Ken (JP)

( * ) Notice: Subject to any disclaimer, the term of this patent is extended or adjusted under 35 U.S.C. 154(b) by 1437 days.

(21) Appl. No.: 10/752,714

(22) Filed: Jan. 8, 2004

(65) Prior Publication Data
US 2004/0193182 A1    Sep. 30, 2004

(30) Foreign Application Priority Data
Jan. 15, 2003 (JP) ............................. 2003-006659
Jun. 25, 2003 (JP) ............................. 2003-181584

(51) Int. Cl.
*A61B 17/32* (2006.01)

(52) U.S. Cl. ...................... 606/169; 606/170

(58) Field of Classification Search ............ 604/19–22, 604/28, 31, 44, 65, 67, 118; 606/42, 169–171, 606/4–6, 10–12, 107, 159, 167; 433/101; 601/2; 600/437, 439, 446, 452
See application file for complete search history.

(56) References Cited
U.S. PATENT DOCUMENTS
5,591,127 A    1/1997   Barwick, Jr. et al.
5,700,240 A *  12/1997  Barwick et al. ............... 604/22
7,077,820 B1 * 7/2006   Kadziauskas et al. ......... 604/22

FOREIGN PATENT DOCUMENTS
JP    05-300921     11/1993
JP    9-508298      8/1997
JP    11-206803     8/1999

OTHER PUBLICATIONS
Japanese Notice of Rejection issued Oct. 17, 2007.
"Invention of an Ultrasonic Apparatus for Cataract Having the Function of Automatic Control of Ultrasonic Pulses" Shigeo Yaguchi et al, Subject No. 189, Japanese Journal of Ophthalmic Surgery, 2003, vol. 16, Extra No., p. 70, Jan. 10, 2003.

* cited by examiner

*Primary Examiner*—Todd E Manahan
*Assistant Examiner*—Christopher Schubert
(74) *Attorney, Agent, or Firm*—Rader, Fishman & Grauer PLLC (57) ABSTRACT

An ultrasonic surgery apparatus enabling smooth surgery. The ultrasonic apparatus is provided with an ultrasonic chip, a vibration inducing unit which induces ultrasonic vibration to the ultrasonic chip, an aspiration unit which aspirates tissue emulsified by vibration of the ultrasonic chip, a detection unit which detects a clogging condition of the ultrasonic chip, a footswitch, having a pedal, for emitting an output signal which is based on a depression amount or a depression position of the pedal, and a control unit which controls at least one of ultrasonic power and a pulse-duty ratio of the ultrasonic vibration based on the output signal from the footswitch and a detection result obtained by the detection unit.

6 Claims, 7 Drawing Sheets

FIG. 11

ULTRASONIC SURGERY APPARATUS

BACKGROUND OF THE INVENTION

1. Field of the Invention

The present invention relates to an ultrasonic surgery apparatus for use in cataract surgery in which an opaque crystalline lens caused by a cataract is subjected to ultrasonic vibrations and emulsified, and then is aspirated and discharged outside a body.

2. Description of Related Art

In cataract surgery, an ultrasonic surgery apparatus is generally widespread which gives ultrasonic vibrations to nucleus of a crystalline lens using a tubular ultrasonic chip (referred to as an US chip, hereinafter) attached to a handpiece for surgery for performing fragmentation and emulsification, and aspirates and removes emulsified tissue of the nucleus of the crystalline lens through an aspiration hole at the tip of the US chip for discharging outside a body. In this kind of apparatus, a surgeon controls operations of irrigation liquid supply to an eye, aspiration, and phacoemulsification (induction of ultrasonic vibrations) using a footswitch having a pedal (see Japanese Patent Application Unexamined Publication No. Hei11-206803).

Besides, an ultrasonic oscillation mode in this kind of apparatus generally includes a pulse oscillation mode in which ultrasonic oscillation and intermission alternate (see WO95/20374 (Japanese Patent Application Unexamined Publication No. Hei9-508298)) in addition to a continuous oscillation mode in which ultrasonic oscillation is successively performed. In the pulse oscillation mode, nucleus followability of the US chip is improved and an amount of ultrasonic wave used is decreased, so that heat production may be suppressed to lower tissue invasion as compared with the continuous oscillation mode. Further, for the apparatus of WO95/20374, ultrasonic power and a pulse-duty ratio at the time of pulse oscillation (the ratio of oscillation to intermission) are changed in accordance with a vacuum (aspiration pressure) level which corresponds to a clogging condition of the US chip.

Incidentally, the ultrasonic power and the pulse-duty ratio are preferably low in view of the tissue invasion because fragmentation power relatively sufficient for soft nucleus of the crystalline lens may thereby be obtained. However, when great fragmentation power is required in such a case where hard nucleus of the crystalline lens is encountered, the conventional apparatus can increase (raise) the ultrasonic power only to a maximum value previously set through an operation panel even if the pedal is depressed. In this occasion, the surgeon instructs an operator of the apparatus (an assistant) to reset and raise the ultrasonic power and the pulse-duty ratio through the operation panel. However, this is troublesome and smooth surgery is difficult to perform.

Additionally, the apparatus of WO95/20374 has a constitution where the ultrasonic power and the pulse-duty ratio are automatically changed according only to the aspiration pressure level. Therefore, the ultrasonic power and the pulse-duty ratio happen to change contrary to the surgeon's intention.

SUMMARY OF THE INVENTION

An object of the invention is to overcome the problems described above and to provide an ultrasonic surgery apparatus which enables a surgeon to increase fragmentation power intentionally in such a case where hard nucleus of a crystalline lens is encountered, and enables smooth surgery.

To achieve the objects and in accordance with the purpose of the present invention, an ultrasonic surgery apparatus includes an ultrasonic chip, a vibration inducing unit which induces ultrasonic vibration to the ultrasonic chip, an aspiration unit which aspirates tissue emulsified by vibration of the ultrasonic chip, a detection unit which detects a clogging condition of the ultrasonic chip, a footswitch, having a pedal, for emitting an output signal which is based on a depression amount or a depression position of the pedal, and a control unit which controls at least one of ultrasonic power and a pulse-duty ratio of the ultrasonic vibration based on the output signal from the footswitch and a detection result obtained by the detection unit.

Additional objects and advantages of the invention are set forth in the description which follows, are obvious from the description, or may be learned by practicing the invention. The objects and advantages of the invention may be realized and attained by the ultrasonic surgery apparatus in the claims.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawings.

DETAILED DESCRIPTION OF THE PREFERRED EMBODIMENTS

Figure 1:
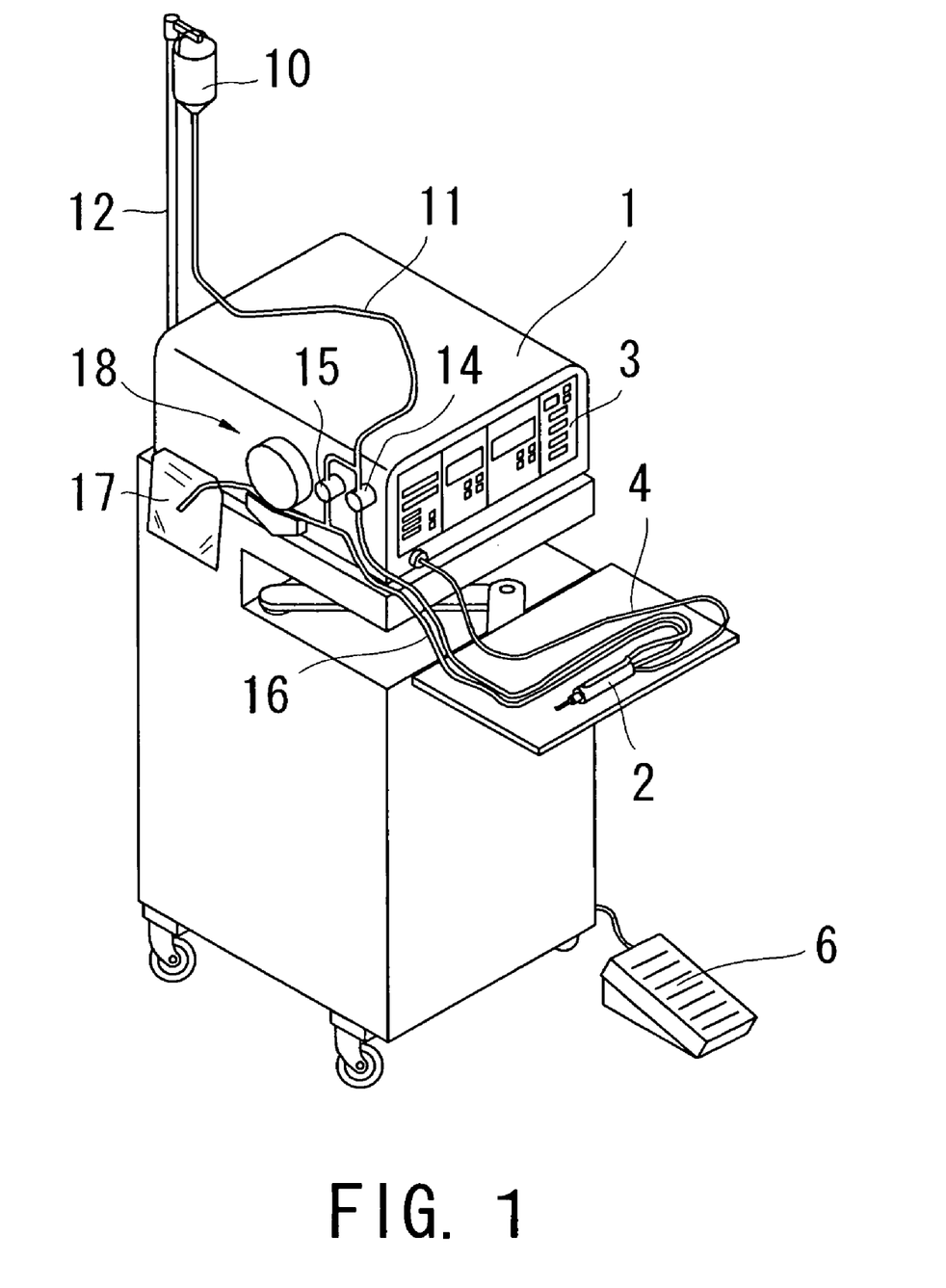
FIG. 1 is a schematic external view of an ultrasonic surgery apparatus.
Figure 2:
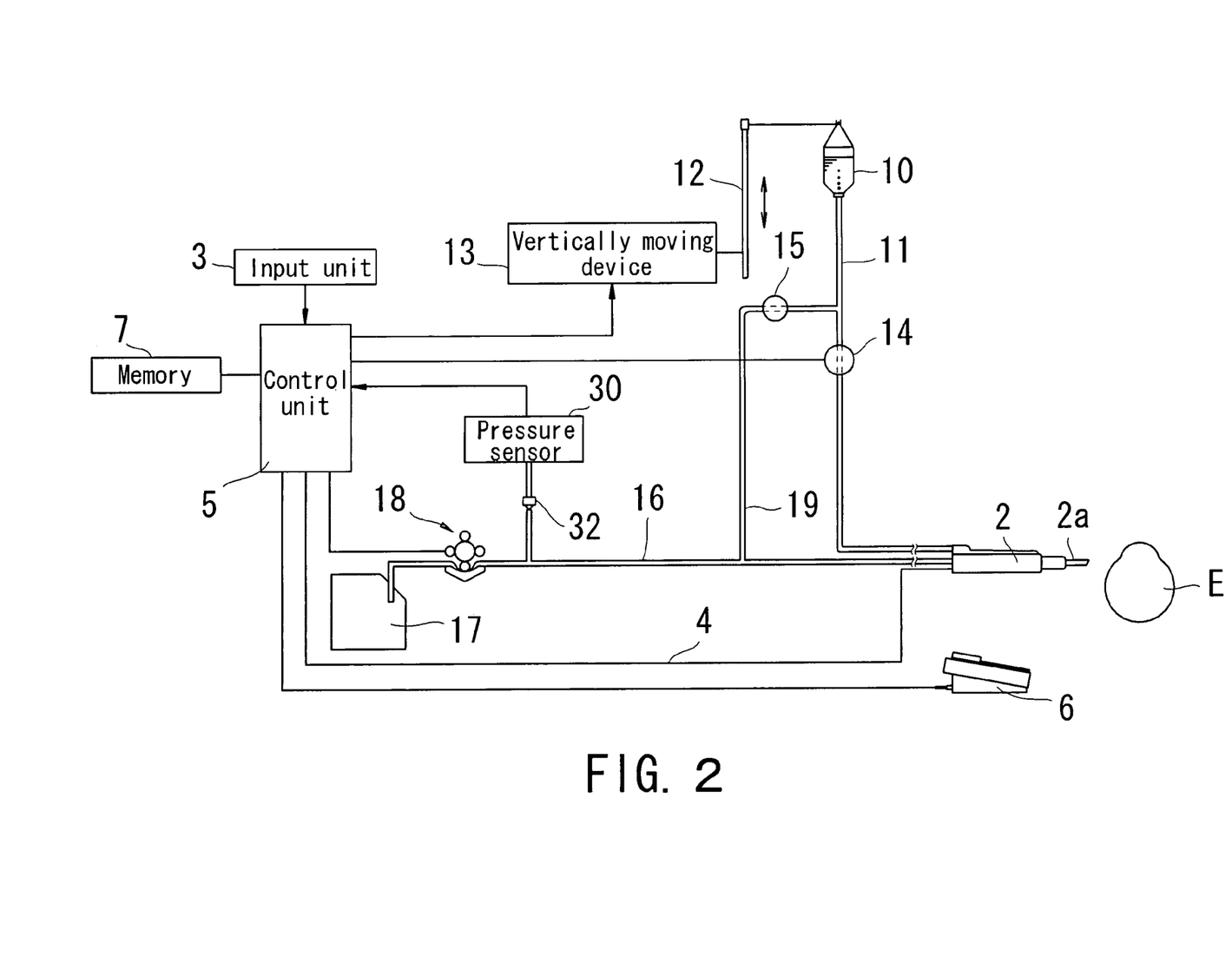
FIG. 2 is a view showing a schematic configuration of the ultrasonic surgery apparatus.

A detailed description of one preferred embodiment of an ultrasonic surgery apparatus embodied by the present invention is provided below with reference to the accompanying drawings. FIG. 1 is a schematic external view of an ultrasonic surgery apparatus. FIG. 2 is a view showing a schematic configuration of the apparatus.

A main body 1 of the apparatus stores a control unit 5 which controls to drive the entire apparatus. An ultrasonic handpiece 2 for surgery (referred to as an US handpiece 2, hereinafter) is held by a surgeon, and a tubular US chip 2a having an aspiration hole is attached to a tip of the US handpiece 2. Ultrasonic vibrations generated by an integrated vibrator in the US handpiece 2 is amplified and conveyed to the US chip 2a. The US chip 2a thereby becomes capable of giving ultrasonic vibrations to nucleus of a crystalline lens for performing fragmentation and emulsification thereon. The vibrator in the US handpiece 2 is provided with driving energy from the control unit 5 in the main body 1 via a cable 4. For the ultrasonic vibrations conveyed to the US chip 2a, a continuous oscillation or a pulse oscillation may be selected, and a switch in an input unit 3 may be used to switch to a mode for either oscillation.

The input part 3 is provided with a switch for altering a combination of irrigation, aspiration, and phacoemulsification in accordance with a depression degree of a pedal of a footswitch 6, and with a group of switches for performing various settings for irrigation pressure, an amount of aspiration flow, aspiration pressure, ultrasonic power, a pulse-duty ratio and the like. Set values inputted through the input unit 3 are stored in a memory 7.

An irrigation bottle 10, filled with an irrigation liquid such as a saline which is supplied to a patient's eye E, is, hanged on a pole 12. The pole 12 is vertically moved by a vertically moving device 13 (or manually moved) so that a height of the bottle 10 may be changed. The height of the bottle 10 is set so as to maintain pressure inside the eye E properly. A control valve 14 is provided midway along an irrigation tube 11 for leading the irrigation liquid to the eye E, and is opened and closed for flow control of the irrigation liquid. One end of the irrigation tube 11 is connected to the bottle 10 and the other end is connected to the US handpiece 2.

An aspiration tube 16 is used to discharge a waste liquid containing the irrigation liquid and the nucleus of the crystalline lens subjected to fragmentation and emulsification aspirated through the aspiration hole of the US chip 2a into a drainage bag 17. Provided midway along the aspiration tube 16 are a connecting part 32 connected to a pressure sensor 30 and a peristaltic aspiration pump 18. Further, the aspiration tube 16 communicates with the irrigation tube 11 via a bypass tube 19, and a control valve 15 is opened and closed for flow control through the bypass tube 19. The aspiration pressure inside the aspiration tube 16 is always detected by the pressure sensor 30. When the aspiration pressure reaches a predetermined (preset) upper limit, the control unit 5 controls to stop the aspiration pump 18. Additionally, in a case where the aspiration pressure should be lowered, the control valve 15 is opened by the control unit 5, and the irrigation liquid is permitted to flow from the irrigation tube 11 via the bypass tube 19 into the aspiration tube 16 for decreasing the aspiration pressure. The upper limit of the aspiration pressure (maximum aspiration pressure) is set with a switch in the input unit 3.

Figure 3:
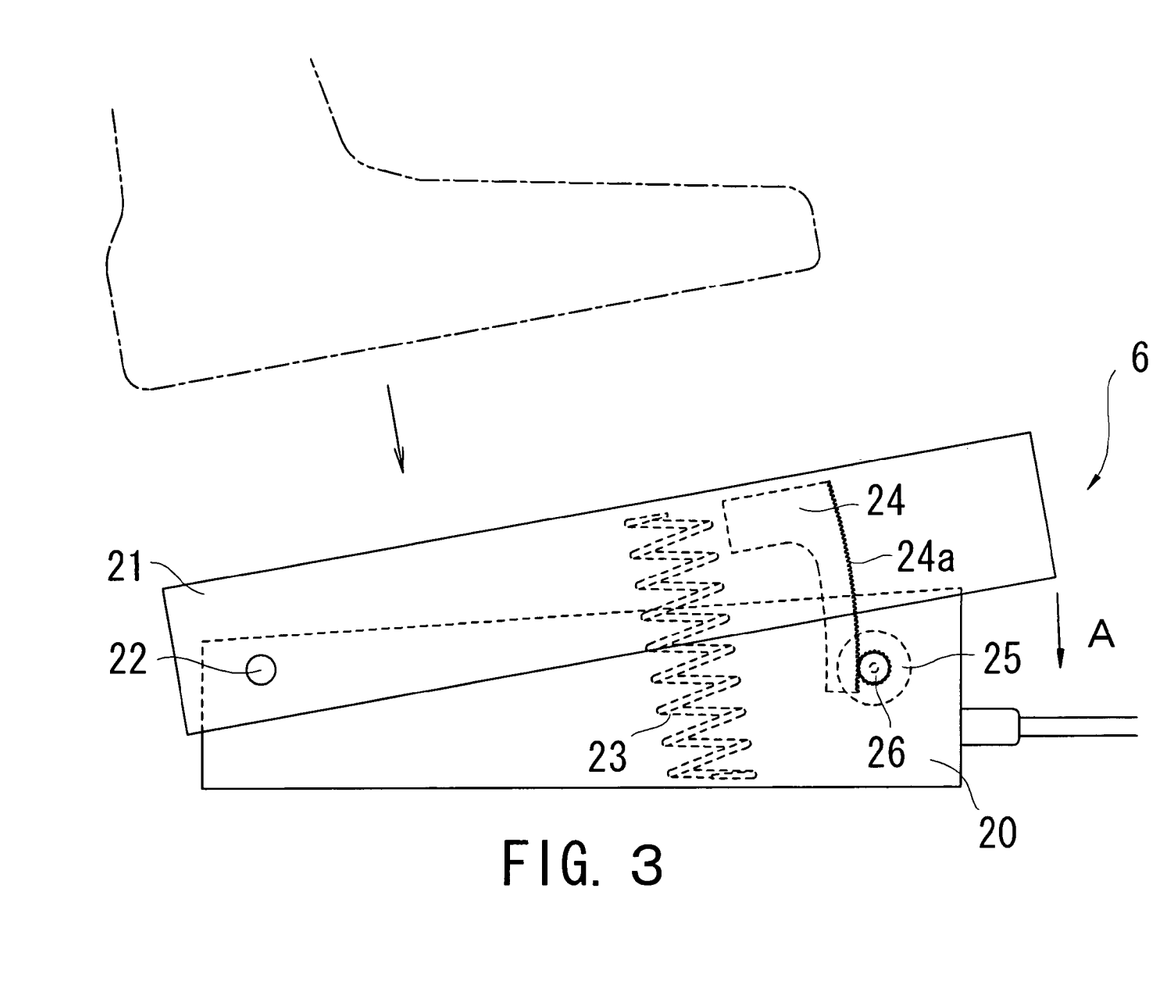
FIG. 3 is a view illustrating a depression mechanism in a footswitch.
Figure 4:
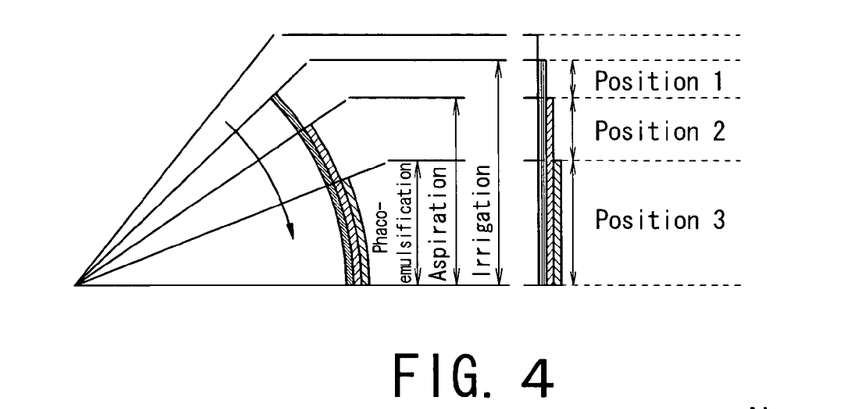
FIG. 4 is a view illustrating operational control of irrigation, aspiration, and phacoemulsification on the basis of a depression amount (depression position) of the footswitch.

FIG. 3 is a view illustrating a depression mechanism in the pedal of the footswitch 6. A rear part of the pedal 21 (a left side of FIG. 3) is coupled to a base part 20 via a shaft 22, and the pedal 21 is rotatable in a direction of the arrow A shown in FIG. 3 about the shaft 22. A spring 23 is interposed between the pedal 21 and the base part 20, and is retained in a state as shown in FIG. 3 when no power is applied to the pedal 21. A conveying element 24 of a depression amount, having a gear part 24a, is fixed inside the pedal 21. A rotational potentiometer 25 is fixed to the base part 20 and a gear 26 in engagement with the gear part 24a of the conveying element 24 is attached to a rotation shaft of the potentiometer 25. When power is applied to the pedal 21, the conveying element 24 is rotated about the shaft 22. This rotation is conveyed via the gear part 24a and the gear 26 to the potentiometer 25, and a depression amount (depression position) of the pedal 21 is detected by the potentiometer 25. And, each operational control of irrigation, aspiration and phacoemulsification (ultrasonic vibrations) is performed in accordance with a signal of the depression amount (depression position) of the pedal 21, of the footswitch 6 (see FIG. 4).

For the apparatus as above, the operation of emulsification and aspiration of the nucleus of the crystalline lens will be described. Incidentally, it is assumed that the upper limit of the aspiration pressure set in the input part 3 is 40 kPa (about 300 mmHg) and the ultrasonic oscillation is set in the pulse oscillation mode.

When a surgeon inserts the US chip 2a of the US handpiece 2 in the eye E and depresses the pedal 21 to a position 1, the control valve 14 is opened under control of the control unit 5 and the irrigation liquid is supplied to the eye E. Next, when the pedal 21 is depressed to a position 2, the aspiration pump 18 is driven under control of the control unit 5, and the waste liquid is aspirated along with the irrigation liquid supply. Further, when the pedal 21 is depressed to a position 3, ultrasonic vibrations are induced to the US chip 2a along with the irrigation and aspiration.

Figure 5:
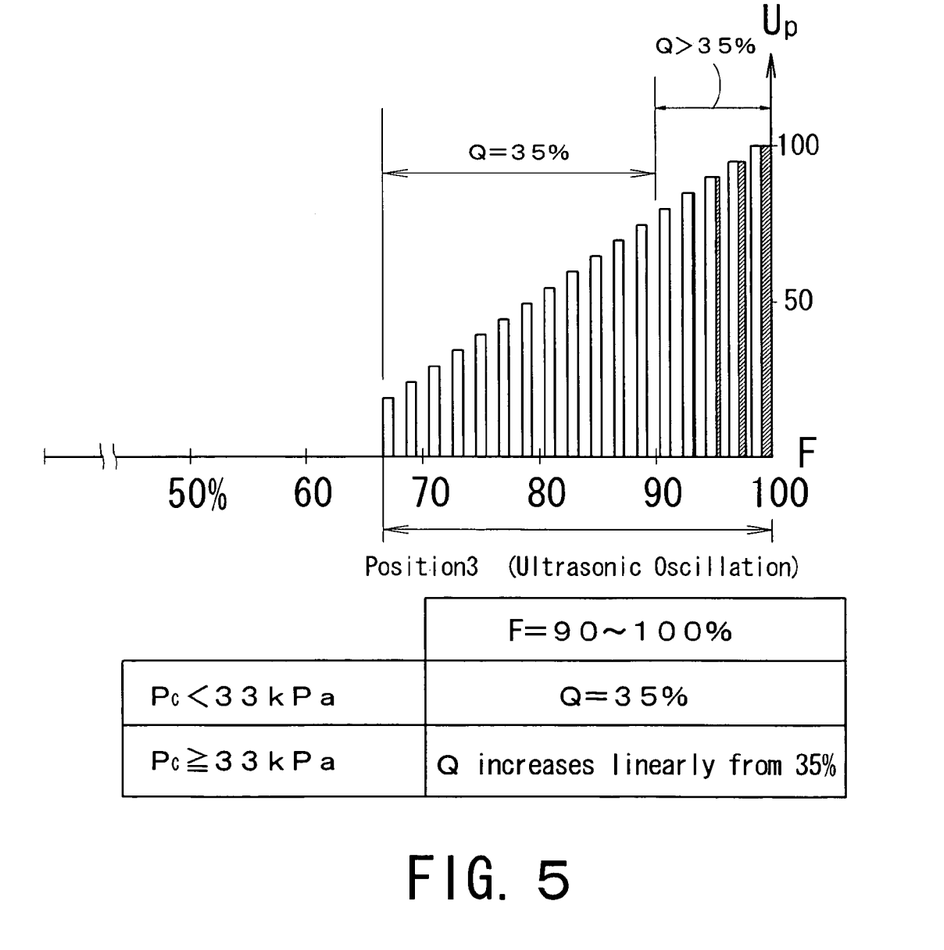
FIG. 5 is a view illustrating a control method of ultrasonic vibrations.

FIG. 5 is a view illustrating a control method of ultrasonic vibrations. Assuming that a depression amount F is 0% when no power is applied to the pedal 21 and the depression amount F is 100% when the pedal 21 is depressed at the maximum, a range of the depression amount F from 66% inclusive to 100% inclusive is set as the position 3 for inducing ultrasonic vibrations. Further, ultrasonic power Up is set so as to increase linearly to an upper limit predetermined in the input unit 3 in accordance with the depression amount F of the pedal 21.

A pulse-duty ratio Q is determined based on the depression amount F of the pedal 21 and aspiration pressure Pc detected by the pressure sensor 30. In a case where the depression amount F is below 90% being a value of predetermined (preset) level, the pulse-duty ratio Q is kept constant at an initial set value Q0 (for example, 35%). In a case where the depression amount F is in a range from 90% being the value of predetermined level inclusive to 100% inclusive, the pulse-duty ratio Q is kept constant at 35% being the initial set value Q0 when the aspiration pressure Pc detected by the pressure sensor 30 is below a value of predetermined (preset) level (for example, 33 kPa (about 250 mmHg)) which is lower than 40 kPa being the upper limit, and the pulse-duty ratio Q is changed to increase linearly in accordance with the depression amount F of the pedal 21 when the aspiration pressured Pc is greater than or equal to 33 kPa being the value of predetermined level. That is to say, the control method of ultrasonic vibrations is changed according to information on whether or not the aspiration pressure Pc is greater than or equal to the value of predetermined level (33 kPa) and information on the depression amount (depression position) of the pedal 21. For instance, when the depression amount F is 90%, the pulse-duty ratio Q is set at 45%, and when the depression amount F is 100%, the pulse-duty ratio F is increased to 70%. In FIG. 5, diagonally shaded areas in a bar graph show an increased amount of the pulse-duty ratio Q from 35% being the initial set value Q0.

In this setting, when the surgeon depresses the pedal 21 to the position 3, ultrasonic vibrations are induced to the US chip 2a to perform fragmentation and emulsification on the nucleus of the crystalline lens. The aspiration pressure Pc detected by the pressures sensor 30 increases if the aspiration hole at the tip of the US chip 2a is clogged with the nucleus of the crystalline lens. In other words, a clogging condition (or a trapping condition of the nucleus of the crystalline lens) at the tip of the US chip 2a is detected from the aspiration pressure Pc. When the nucleus of the crystalline lens is relatively soft, it is easy to emulsify; therefore, the aspiration pressure Pc is not so significantly increased and the nucleus of the crystalline lens trapped at the tip of the US chip 2a is emulsified and aspirated. When the nucleus of the crystalline lens is relatively hard, the depression amount F of the pedal 21 is increased to raise the ultrasonic power Up so that emulsifying efficiency is enhanced. The surgeon increases the depression amount F of the pedal 21 at the time when he/she intends to expand capacity for fragmentation and emulsification.

Here, in a case where the relatively hard nucleus of the crystalline lens is encountered and the nucleus of the crystalline lens trapped at the tip of the US chip 2a is not easily emulsified and aspirated, the aspiration pressure Pc is increased. When the aspiration pressure Pc does not reach 40 kPa being the upper limit but is greater than or equal to 33 kPa being the value of predetermined level as well as when the depression amount F of the pedal 21 is greater than or equal to 90% being the value of predetermined level, the control unit 5 controls to increase the pulse-duty ratio Q from 35% being the initial set value Q0 in accordance with the increase in the depression amount F. The pulse-duty ratio Q is increased, and energy of ultrasonic vibrations given to the nucleus of the crystalline lens in a predetermined period of time is increased. Therefore, the nucleus of the crystalline lens may be efficiently subjected to fragmentation and emulsification.

As the nucleus of the crystalline lens, which has clogged the aspiration hole at the tip of the US chip 2a, is subjected to fragmentation and starts to be aspirated, the aspiration pressure Pc is also decreased. When the aspiration pressure Pc becomes less than or equal to 33 kPa being the value of predetermined level, the pulse-duty ratio Q is restored to 35% being the initial set value Q0. In the case of the relatively soft nucleus of the crystalline lens and the like for which high fragmentation power is not required, decrease in the pulse-duty ratio Q suppresses an amount of ultrasonic wave used as well as heat production to the tissue.

As mentioned above, when the aspiration pressure Pc is greater than or equal to 33 kPa being the value of predetermined level, i.e. when the nucleus of the crystalline lens is sufficiently trapped by the US chip 2a, the surgeon may increase the fragmentation and emulsification power by regulating the depression degree of the pedal 21, and the intention of the surgeon may be reflected with ease. On the other hand, when the aspiration pressure Pc is below 33 kPa being the value of predetermined level, the fragmentation and emulsification power is sufficient, and the amount of ultrasonic wave used need not be excessively increased.

Figure 6:
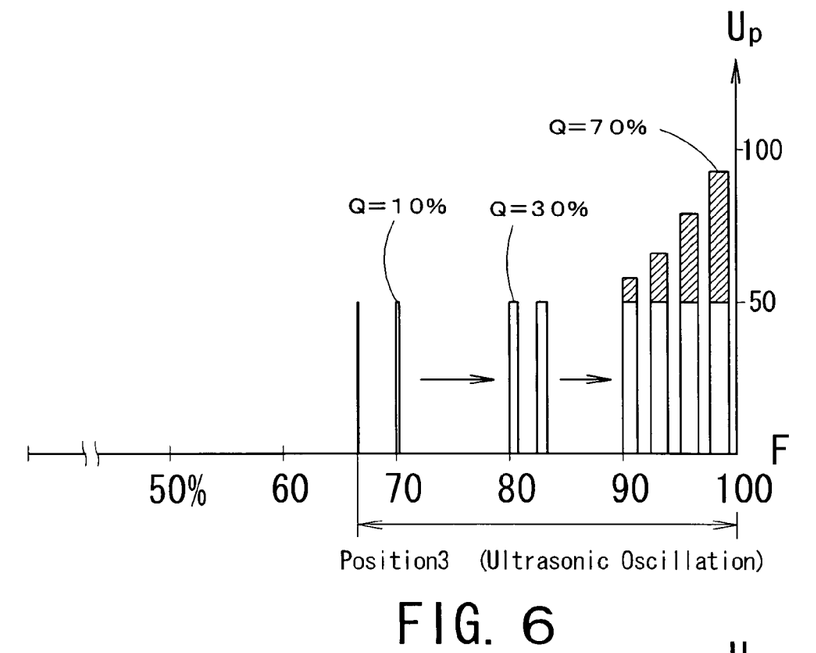
FIG. 6 is a view illustrating another control method of ultrasonic vibrations.

FIG. 6 is a view showing another control method of ultrasonic vibrations. In this control, when the aspiration pressure Pc in the position 3 is below 33 kPa being the value of predetermined level, the ultrasonic power Up is kept constant at an initial set value U0 (for example, 50%), and the pulse-duty ratio Q is increased in stages (or linearly) to 70% in accordance with the depression amount F of the pedal 21. Further, in the range of the depression amount F from 90% being the value of predetermined level inclusive to 100% inclusive, when the aspiration pressure Pc is greater than or equal to 33 kPa being the value of predetermined level, the ultrasonic power Up is linearly increased from 50% being the initial set value U0 in accordance with the depression amount F. In addition, when the depression amount F is 100%, the ultrasonic power Up is set at 100% being the upper limit.

Figure 7:
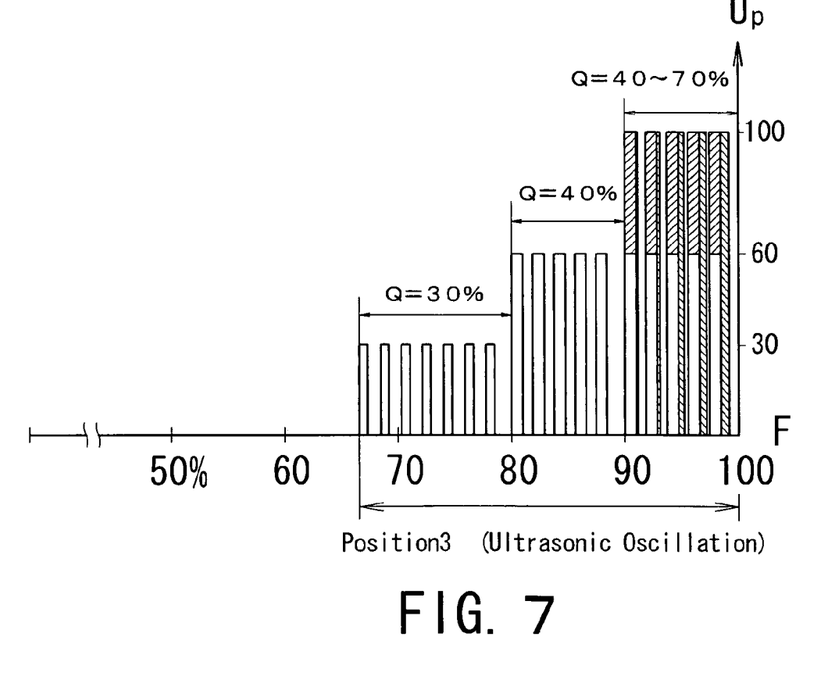
FIG. 7 is a view illustrating still another control method of ultrasonic vibrations.

FIG. 7 is a view illustrating an example of a control method where both the ultrasonic power Up and the pulse-duty ratio Q are changed in accordance with the depression amount F of the pedal 21 in the position 3 when the aspiration pressure Pc is greater than or equal to 33 kPa being the value of predetermined level. For example, when the depression amount F is in a range from 70% inclusive and 80% exclusive, the pulse-duty ratio Q is 30% and the ultrasonic power Up is 30%. When the depression amount F is in a range from 80% inclusive to 90% exclusive, the pulse-duty ratio Q is 40% and the ultrasonic power Up is 60%. In addition, in the range, of the depression amount F from 90% being the value of predetermined level inclusive to 100% inclusive, when the aspiration pressure Pc is below 33 kPa being the value of predetermined level, the ultrasonic power Up and the pulse-duty ratio Q are the same as in a case where the depression amount F is in the range from 80% inclusive to 90% exclusive. However, when the aspiration pressure Pc is greater than or equal to 33 kPa being the value of predetermined level, as shown by diagonally shaded areas in FIG. 7, the ultrasonic power Up is increased to 100% as well as the pulse-duty ratio Q is linearly increased in a range from 40% inclusive to 70% inclusive (or exclusive) in accordance with the depression amount F of the pedal 21.

Also in the control methods shown in FIGS. 6 and 7, when the hard nucleus of the crystalline lens is encountered and the aspiration pressure Pc becomes greater than or equal to 33 kPa being the value of predetermined level, the surgeon may intentionally depress the pedal 21 to increase the fragmentation and emulsification power.

Besides, the value of predetermined level of the aspiration pressure Pc when the ultrasonic power Up and the pulse-duty ratio Q are changed is mentioned above, but this is only an illustration, and the surgeon may set a desired value as the value of predetermined level of the aspiration pressure Pc in relation to the value for the upper limit using the input unit 3. The value of predetermined level of the aspiration pressure Pc may also be set in association with the value for the upper limit, such as 80% of the upper value. Further, the maximum value of the ultrasonic power Up may be arbitrarily changed by the input unit 3 so as to be, for example, 50% when the depression amount F of the pedal 21 is 100%. Furthermore, while the value of predetermined level of the depression amount F when the ultrasonic power Up and the pulse-duty ratio Q are changed is set at 90%, it may be arbitrarily changed by the input unit 3.

Additionally, the aforementioned control methods may be variously modified. For example, in the control method shown in FIG. 5, when the aspiration pressure Pc is greater than or equal to 33 kPa being the value of predetermined level, it is conceivable that the pulse-duty ratio Q is uniformly set at 70% in the range of the depression amount F of the pedal 21 from 90% being the value of predetermined level inclusive to 100% inclusive. Further, an inducing condition of ultrasonic vibrations may be controlled more finely such that a plurality of the aspiration pressure Pc, when the ultrasonic power Up and the pulse-duty ratio Q are increased, is previously set, and the ultrasonic power Up and the pulse-duty ratio Q are increased for each set aspiration pressure Pc. In addition, this kind of control is not limited to the pulse oscillation mode, and may be applied to control of only the ultrasonic power Up in the continuous oscillation mode.

Further, in the above description, the aspiration pressure Pc obtained by the pressure sensor 30 is utilized as means for detecting the clogging condition at the tip of the US chip 2a. However, a constitution may be employed such that an image-pickup camera for observing the eye E is attached to a surgical microscope, and the clogging condition at the tip of the US chip 2a is detected from an image obtained by the camera.

In the above description, a condition is made that the control method of ultrasonic vibrations through the ultrasonic power Up and the pulse-duty ratio Q is changed when the aspiration pressure Pc is greater than or equal to the value of predetermined level (a lower value than the value for the upper limit) and the depression amount (depression position) of the pedal 21 is greater than or equal to the value of predetermined level. However, another changing condition may be made on whether the depression amount (depression position) of the pedal 21 is kept constant longer than period of time of predetermined (preset) level. Hereinafter, the control method of ultrasonic vibrations under this changing condition will be described.

Figure 8:
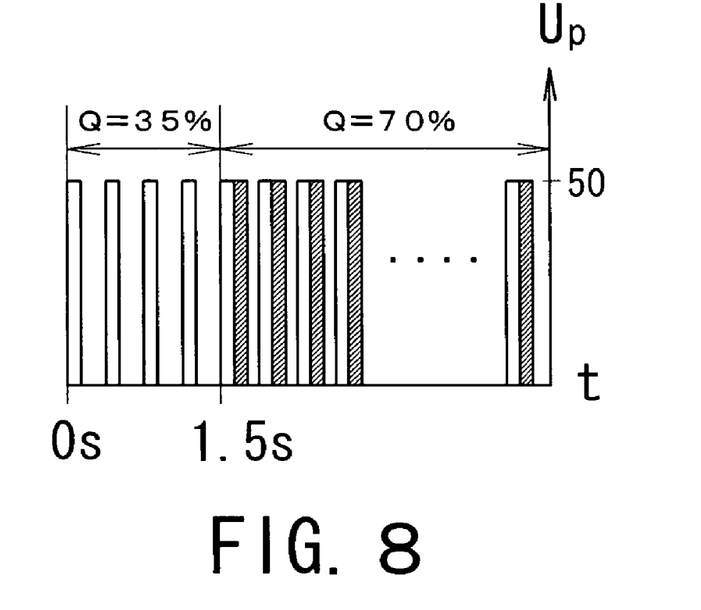
FIG. 8 is a view illustrating still another control method of ultrasonic vibrations.

FIG. 8 is a view illustrating an example where the pulse-duty ratio Q is changed based on a time t during which the depression amount (depression position) F of the pedal 21 is kept constant. The control unit 5 controls to start measurement of the time t from a point when the depression amount F of the pedal 21 becomes constant based on an output of the potentiometer 25 and reset the time, t in a case where the depression amount F is changed. Besides, the ultrasonic power Up, as in the case of FIG. 5, is linearly changed in accordance with the depression amount F. When the nucleus of the crystalline lens trapped at the tip of the US chip 2a is not emulsified and aspirated, the aspiration pressure Pc is increased. When the aspiration pressure Pc becomes greater than or equal to 33 kPa being the value of predetermined level, the US chip 2a is judged to be in the clogging condition produced by attraction for the nucleus of the crystalline lens. Here, the pedal 21 is, for example, assumed to be retained by the surgeon in a position of the depression amount F of about 80% in which the ultrasonic power Up is 50%. The control unit 5 controls to increase the pulse-duty ratio Q from 35% to 70% when the time t, during which the depression amount F of the pedal 21 is kept constant, is greater than or equal to a value of predetermined (preset) level (for example, one and a half seconds). The pulse-duty ratio Q is increased to raise the fragmentation power and enable efficient fragmentation and emulsification of the nucleus of the crystalline lens. If the fragmentation and emulsification of the nucleus of the crystalline lens make the aspiration pressure Pc below 33 kPa being the value of predetermined level, the pulse-duty ratio Q is restored to 35% being the initial set value. That is, the initial control method is restored. In addition, when the surgeon changes the depression amount F of the pedal 21 as well, the control unit 5 controls to reset measurement of the time t and restore the pulse-duty ratio Q to 35% being the initial set value.

Figure 9:
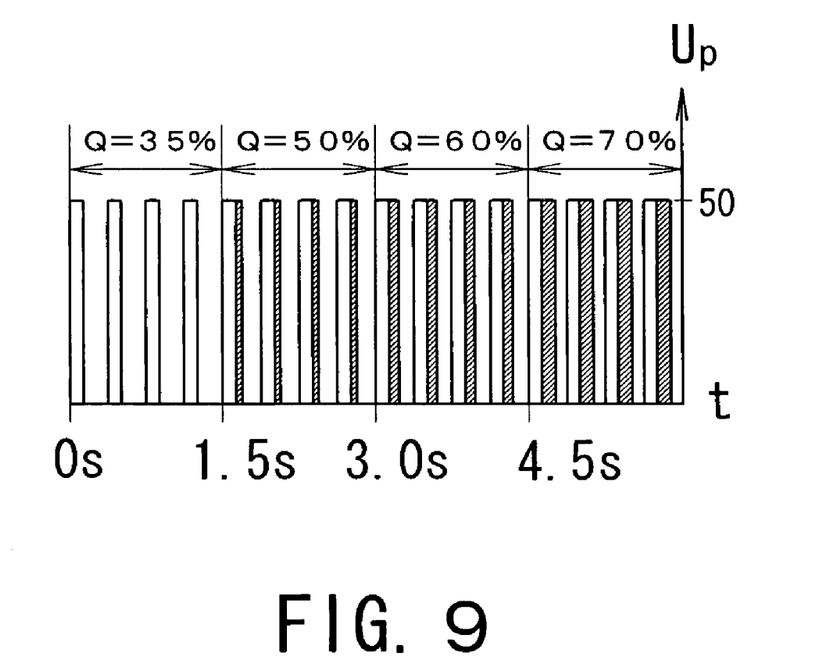
FIG. 9 is a view illustrating still another control method of ultrasonic vibrations.

FIG. 9 shows a modification of the control method for changing the pulse-duty ratio Q. A control method may be made such that, when the time t is greater than or equal to one and a half seconds being the value of predetermined level, the pulse-duty ratio Q is increased in stages (or linearly) in accordance with an elapsed time thereafter.

Figure 10A:
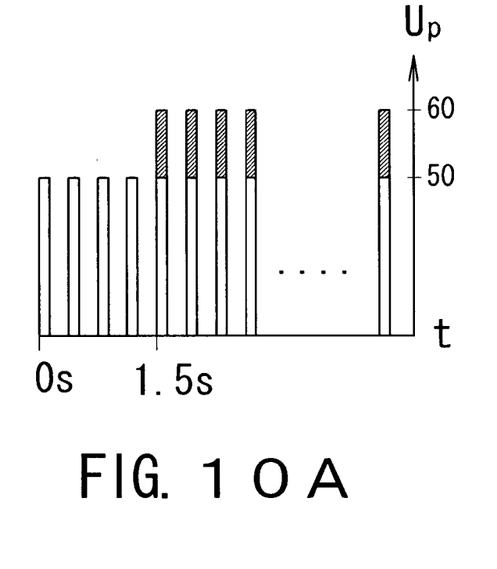
FIGS. 10A and 10B are views illustrating still other control methods of ultrasonic vibrations.
Figure 10B:
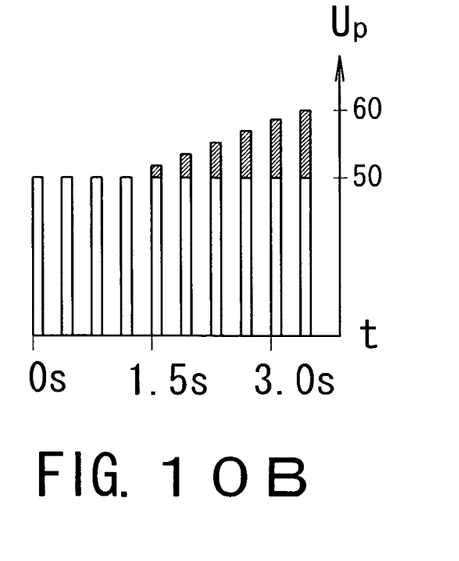

FIGS. 10A and 10B are views illustrating an example of control methods for changing the ultrasonic power up based on the time t during which the depression amount F is kept constant. In FIG. 10A, when the aspiration pressure Pc is greater than or equal to 33 kPa being the value of predetermined level as well as when the time t is greater than or equal to one and a half seconds being the value of predetermined level, the ultrasonic power Up is increased by 10% from the ultrasonic power Up for the depression amount F. In FIG. 10B, as in the case of FIG. 10A, when the aspiration pressure Pc is greater than or equal to 33 kPa being the value of predetermined level as well as when the time t is greater than or equal to one and a half seconds being the value of predetermined level, the ultrasonic power Up is linearly increased in accordance with an elapsed time thereafter.

Figure 11:
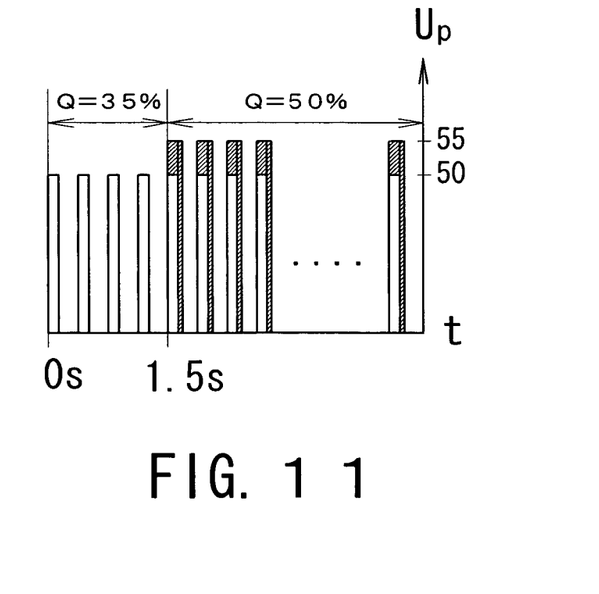
FIG. 11 is a view illustrating still another control method of ultrasonic vibrations.

FIG. 11 is a view illustrating an example of a control method for changing both the ultrasonic power Up and the pulse-duty ratio Q based on the time t during which the depression amount F is kept constant. When the aspiration pressure Pc is greater than or equal to 33 kPa being the value of predetermined level and the time t is greater than or equal to one and a half seconds being the value of predetermined level, the ultrasonic power Up is increased by 5% from the ultrasonic power Up for the depression amount F, and the pulse-duty ratio Q is increased from 35% to 50%.

In the control methods shown in FIGS. 5 to 7, if the hard nucleus is encountered, the pedal 21 must be depressed greater than or equal to an amount for the predetermined (preset) level in order to increase the fragmentation power. In contrast, in the control methods shown in FIGS. 8 to 11, the fragmentation power may be increased regardless of the depression amount (depression position) of the pedal 21. Therefore, a same advantage may be obtained by only keeping the amount (position) for the predetermined level constant without depressing the pedal 21 greatly.

Incidentally, in the above description, the respective values for the depression amount (depression position) F, the aspiration pressure Pc, the ultrasonic power Up, the pulse-duty ratio Q, and the time t may be changed through the input unit 3. Further, a switch provided to the input unit 3 may be used to select from a variety of control methods of ultrasonic vibrations as mentioned above. In this case, a mode is included where the aforementioned methods are not used.

As mentioned above, according to the present invention, when the hard nucleus of the crystalline lens is encountered and is sufficiently trapped by the ultrasonic chip, the surgeon may increase the power for the fragmentation and emulsification intentionally to enable smooth surgery.

The foregoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. An ultrasonic surgery apparatus comprising:
   an ultrasonic chip;
   a vibration inducing unit which induces ultrasonic vibration to the ultrasonic chip;
   an aspiration unit which aspirates tissue emulsified by vibration of the ultrasonic chip;
   a detection unit which includes a pressure sensor for detecting aspiration pressure of the aspiration unit and detects a clogging condition of the ultrasonic chip;
   a footswitch, having a pedal, for emitting an output signal which is based on a depression amount or a depression position of the pedal; and
   a control unit which controls at least one of ultrasonic power and a pulse-duty ratio of the ultrasonic vibration based on the output signal from the footswitch and a detection result obtained by the detection unit, wherein
   the control unit controls the ultrasonic vibration by a first control method when the depression amount or the depression position reaches a predetermined level as well as when the aspiration pressure does not reach the predetermined level, and controls the ultrasonic vibration by a second control method, which is different from the first control method, when the depression amount or the depression position reaches the predetermined level as well as when the aspiration pressure reaches the predetermined level, the first control method keeps the pulse-duty ratio constant regardless of a change in the depression amount or the depression position, and the second control method changes the pulse-duty ratio linearly or in stages in accordance with the change in the depression amount or the depression position.

2. The ultrasonic surgery apparatus according to claim 1, wherein the first and second control methods change the ultrasonic power linearly or in stages in accordance with the change in the depression amount or the depression position.

3. An ultrasonic surgery apparatus comprising:

an ultrasonic chip;

a vibration inducing unit which induces ultrasonic vibration to the ultrasonic chip;

an aspiration unit which aspirates tissue emulsified by vibration of the ultrasonic chip;

a detection unit which includes a pressure sensor for detecting aspiration pressure of the aspiration unit and detects a clogging condition of the ultrasonic chip;

a footswitch, having a pedal, for emitting an output signal which is based on a depression amount or a depression position of the pedal; and a control unit which controls at least one of ultrasonic power and a pulse-duty ratio of the ultrasonic vibration based on the output signal from the footswitch and a detection result obtained by the detection unit, wherein the control unit controls the ultrasonic vibration by a first control method when the depression amount or the depression position reaches a predetermined level as well as when the aspiration pressure does not reach the predetermined level, and controls the ultrasonic vibration by a second control method, which is different from the first control method, when the depression amount or the depression position reaches the predetermined level as well as when the aspiration pressure reaches the predetermined level, the first control method keeps the ultrasonic power constant regardless of a change in the depression amount or the depression position, and the second control method changes the ultrasonic power linearly or in stages in accordance with the change in the depression amount or the depression position.

4. The ultrasonic surgery apparatus according to claim 3, wherein the first and second control methods change the pulse-duty ratio linearly or in stages in accordance with the change in the depression amount or the depression position.

5. An ultrasonic surgery apparatus comprising:

an ultrasonic chip;

a vibration inducing unit which induces ultrasonic vibration to the ultrasonic chip;

an aspiration unit which aspirates tissue emulsified by vibration of the ultrasonic chip;

a detection unit which includes a pressure sensor for detecting aspiration pressure of the aspiration unit and detects a clogging condition of the ultrasonic chip;

a footswitch, having a pedal, for emitting an output signal which is based on a depression amount or a depression position of the pedal; and a control unit which controls at least one of ultrasonic power and a pulse-duty ratio of the ultrasonic vibration based on the output signal from the footswitch and a detection result obtained by the detection unit, wherein the control unit changes the control method of the ultrasonic vibration based on a time during which the depression amount or the depression position is kept constant when the detected aspiration pressure reaches the predetermined level.

6. The ultrasonic surgery apparatus according to claim 5, wherein, when the detected aspiration pressure reaches the predetermined level, the control unit controls the ultrasonic vibration by a first control method when the time during which the depression amount or the depression position is kept constant does not reach a predetermined level, and controls the ultrasonic vibration by a second control method, which is different from the first control method, when the time during which the depression amount or the depression position is kept constant reaches the predetermined level.

* * * * *